(12) United States Patent
Osadchy et al.

(10) Patent No.: US 11,213,235 B2
(45) Date of Patent: Jan. 4, 2022

(54) CORONARY SINUS (CS) CATHETER MOVEMENT DETECTION

(71) Applicant: BIOSENSE WEBSTER (ISRAEL) LTD., Yokneam (IL)

(72) Inventors: Daniel Osadchy, Haifa (IL); Meir Bar-Tal, Haifa (IL); Shmuel Auerbach, Kerem Maharal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 230 days.

(21) Appl. No.: 16/209,418

(22) Filed: Dec. 4, 2018

(65) Prior Publication Data

US 2020/0170525 A1    Jun. 4, 2020

(51) Int. Cl.
| | | |
|---|---|---|
| *A61B 5/28* | (2021.01) | |
| *A61B 5/283* | (2021.01) | |
| *A61B 5/00* | (2006.01) | |
| *A61B 5/06* | (2006.01) | |
| *A61B 18/14* | (2006.01) | |
| *A61B 18/00* | (2006.01) | |

(52) U.S. Cl.
CPC ............ *A61B 5/283* (2021.01); *A61B 5/0084* (2013.01); *A61B 5/061* (2013.01); *A61B 5/068* (2013.01); *A61B 5/6852* (2013.01); *A61B 18/1492* (2013.01); *A61B 2018/00351* (2013.01)

(58) Field of Classification Search
None
See application file for complete search history.

(56) References Cited

U.S. PATENT DOCUMENTS

| | | |
|---|---|---|
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 8,725,240 B2 | 5/2014 | Harlev et al. |
| 9,585,586 B2 | 3/2017 | Schweitzer et al. |

(Continued)

FOREIGN PATENT DOCUMENTS

EP    2000088 A1    12/2008

OTHER PUBLICATIONS

European Search Report for corresponding EPA No. 19213218.1 dated Apr. 29, 2020.

(Continued)

*Primary Examiner* — Ankit D Tejani
(74) *Attorney, Agent, or Firm* — Dergosits & Noah LLP; Todd A Noah

(57) ABSTRACT

A method includes receiving (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS. An electrophysiological (EP) map of at least part of the heart is calculated by time-referencing the ECG signals relative to the reference ECG signal. Based on the position signals, a displacement of the reference catheter from the nominal location in the CS, which distorts the time-referencing, is estimated. The distortion in the EP map is mitigated using the estimated displacement.

14 Claims, 3 Drawing Sheets

(56) References Cited

U.S. PATENT DOCUMENTS

| | | |
|---|---|---|
| 2008/0161681 A1 | 7/2008 | Hauck |
| 2009/0030307 A1* | 1/2009 | Govari ..................... A61B 5/06 |
| | | 600/424 |
| 2012/0172702 A1 | 7/2012 | Koyrakh et al. |
| 2018/0132938 A1 | 5/2018 | Everling |
| 2019/0069954 A1* | 3/2019 | Cohen ................... A61B 6/503 |

OTHER PUBLICATIONS

St. Jude et al., "EnSite Precision (TM) Cardiac Mapping System Model EE3000 Instructions for Use International Edition", p. 1200, Jan. 12, 2016.

* cited by examiner

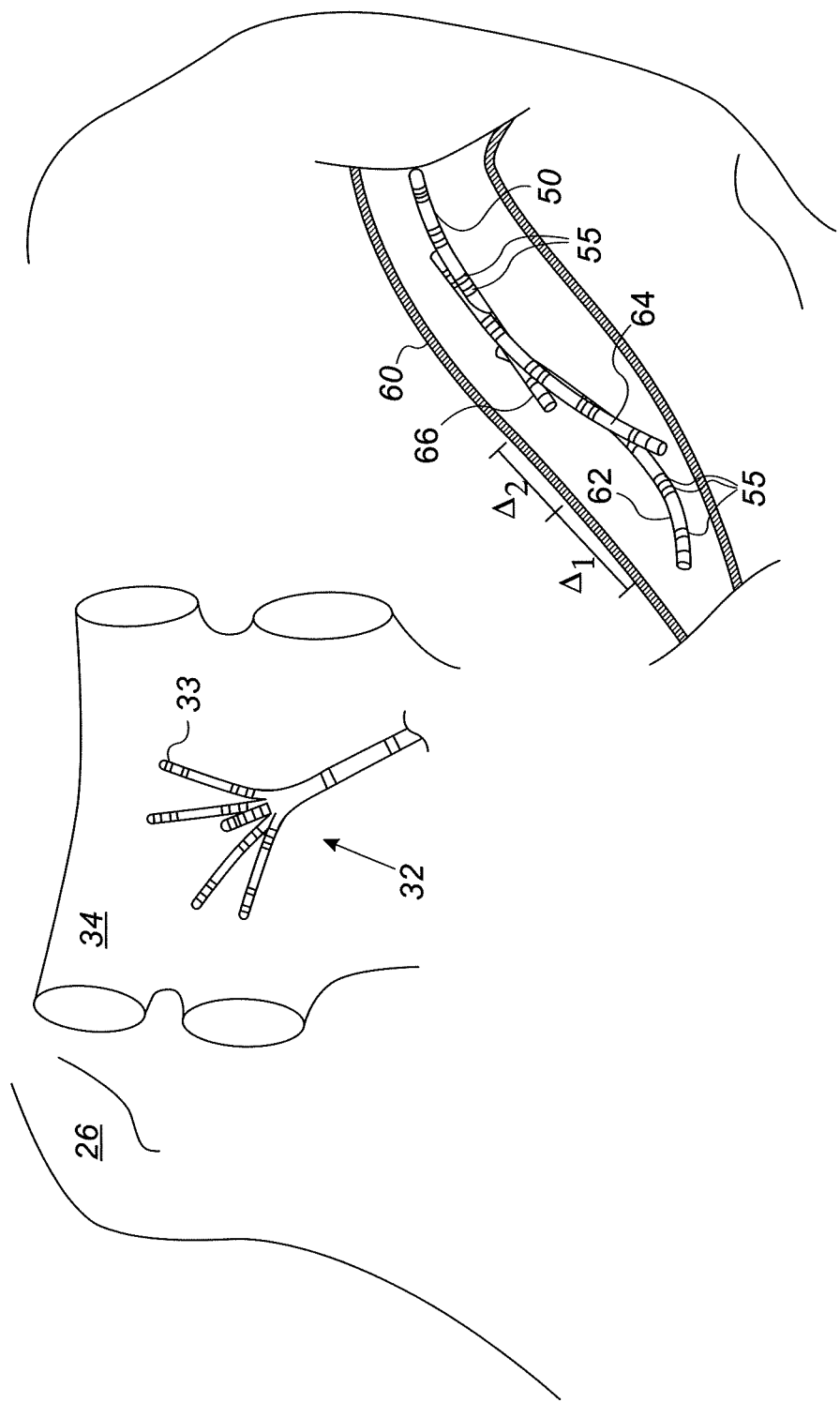

CORONARY SINUS (CS) CATHETER MOVEMENT DETECTION

FIELD OF THE INVENTION

The present invention relates generally to sensing a position of an object placed within a living body, and specifically to providing an accurate intracardiac reference signal for intracardiac electrophysiological mapping.

BACKGROUND OF THE INVENTION

Invasive cardiology techniques involving tracking a position of cardiac catheters has been previously proposed in the patent literature. For example, U.S. Patent Application Publication 2008/0161681 describes a method of tracking a three-dimensional (3D) position of a catheter within a patient including securing a navigational reference at a reference location within the patient. The method further includes defining the reference location as the origin of a coordinate system, determining a location of an electrode moving within the patient relative to that coordinate system, and monitoring for a dislodgement of the navigational reference from the initial reference location. For example, the dislodgement is monitored by measuring the navigational reference relative to a far field reference outside the patient's body, and generating a signal indicating that the navigational reference has dislodged from the reference location. Upon dislodgement, a user may be provided with guidance to help reposition and secure the navigational reference to the initial reference location. Alternatively, the navigational reference may be automatically repositioned and secured to the initial reference location. Alternatively, a reference adjustment may be calculated to compensate for the changed reference point/origin.

As another example, U.S. Patent Application Publication 2018/0132938 describes a method for aligning a cardiac model including receiving an initial position signal from three position sensors disposed along a distal end of a coronary sinus catheter positioned in a coronary sinus of a heart. The method can further include receiving a subsequent position signal from the three position sensors. The method can include determining a positional change vector based on a change in position between an initial position associated with the initial position signal and a subsequent position associated with the subsequent position signal. The method can also include shifting a point of interest associated with a cardiac model, using the positional change vector. The method can include dynamically aligning the cardiac model based on an updated position of the three position sensors.

SUMMARY OF THE INVENTION

An embodiment of the present invention provides a method including receiving (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS. An electrophysiological (EP) map of at least part of the heart is calculated by time-referencing the ECG signals relative to the reference ECG signal. Based on the position signals, a displacement of the reference catheter from the nominal location in the CS, which distorts the time-referencing, is estimated. The distortion in the EP map is mitigated using the estimated displacement.

In some embodiments, the method further includes producing the position signals by performing electrical measurements between the reference catheter and multiple electrodes attached to the body of the patient.

In some embodiments, performing the electrical measurement includes performing one of current measurements, voltage measurements, and impedance measurements.

In an embodiment, estimating the displacement includes calculating the displacement using an empirical formula that translates the electrical measurements to the displacement.

In another embodiment, the method further includes presenting to a user a magnitude and a direction of the displacement.

In some embodiments, mitigating the distortion includes prompting a user to move the reference catheter to the nominal location.

In some embodiments, mitigating the distortion includes adapting the ECG signals, or the EP map, to compensate for the displacement of the reference catheter.

There is additionally provided, in accordance with an embodiment of the present invention, a system including an electrical interface and a processor. The electrical interface is configured to receive (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS. The processor is configured to: (a) calculate an electrophysiological (EP) map of at least part of the heart, by time-referencing the ECG signals relative to the reference ECG signal, (b) based on the position signals, estimate a displacement of the reference catheter from the nominal location in the CS, which distorts the time-referencing, and (c) mitigate the distortion in the EP map using the estimated displacement.

The present invention will be more fully understood from the following detailed description of the embodiments thereof, taken together with the drawings in which:

BRIEF DESCRIPTION OF THE DRAWINGS

FIG. 2 is a schematic detail view showing an EP mapping catheter and a coronary sinus (CS) catheter inside a heart, in accordance with an embodiment of the present invention;

DETAILED DESCRIPTION OF EMBODIMENTS

Overview

Figure 1:
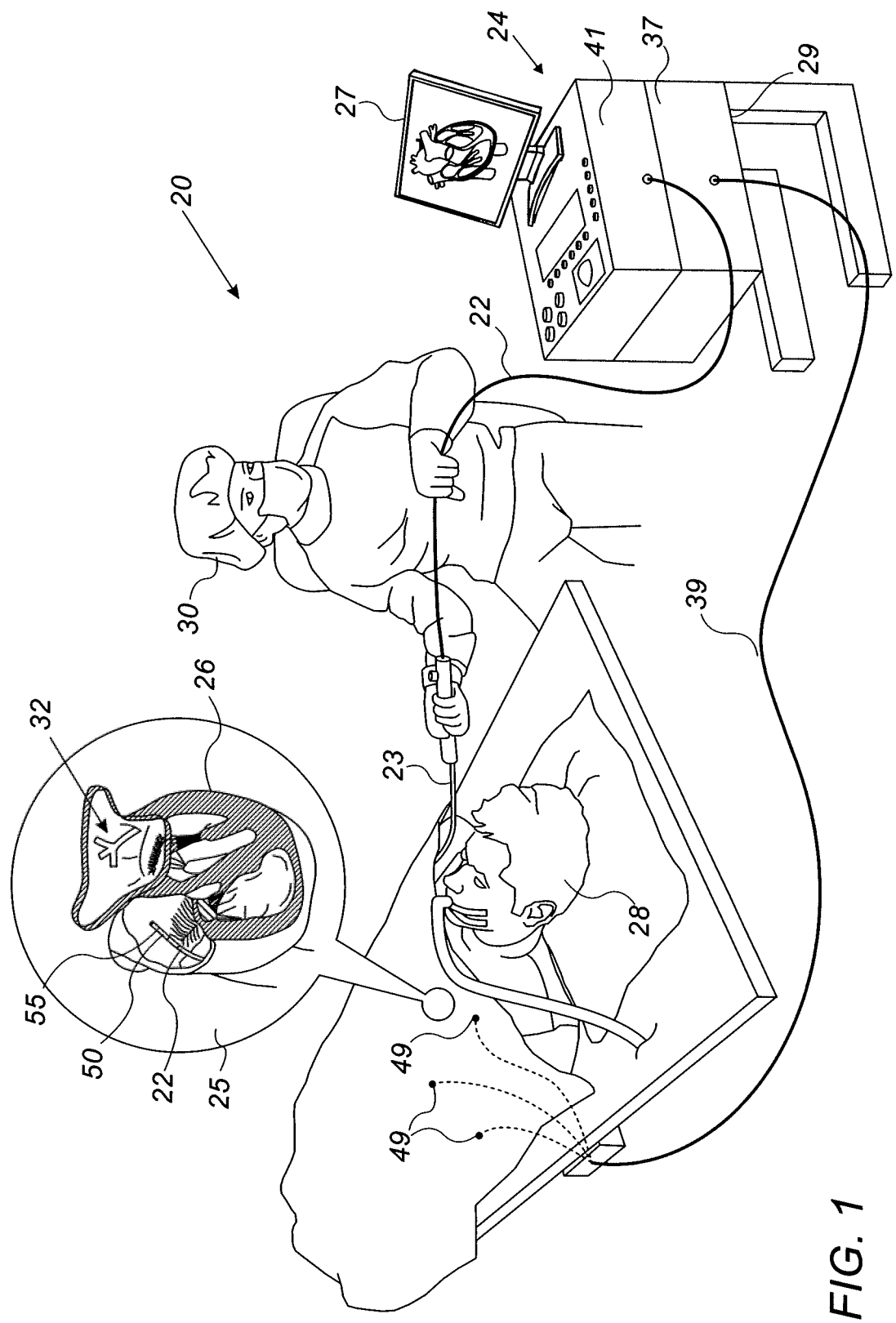
FIG. 1 is a schematic, pictorial illustration of an electrophysiological (EP) mapping system, in accordance with an embodiment of the present invention.

Intracardiac electrophysiological (EP) mapping (also named herein "electroanatomical mapping") is a catheter-based method that may be applied to characterize cardiac EP abnormalities of a patient, such as an arrhythmia. In intra-cardiac EP mapping, the analyzed EP signals are assumed to be intra-cardiac electrocardiogram (ECG) potential-time relationships. In order to fully characterize such relationships, the signals at various intra-cardiac locations need to be referenced in time to each other. The time referencing is accomplished by annotating measured signals relative to a reference-time (e.g., an instance), such as the beginning of each QRS complex of an ECG reference signal (i.e., the beginning of every heartbeat).

Based on time referencing (e.g., annotating) the ECG signals with the timings of the acquired reference signal, a processor analyzes the propagation paths and velocities of EP potentials in the heart and produce an EP map that a physician can analyze to diagnose the patient. A method for generating an EP map is described in U.S. Pat. No. 9,050,011, whose disclosure is fully incorporated herein by reference.

In some embodiments, during an electro-anatomical mapping session, a mapping-catheter moves in a cardiac chamber and measures EP signals, such as ECG signals, at respectively measured intracardiac locations. At the same time, a reference catheter comprising a sensing-electrode, such as a coronary sinus (CS) catheter, is statically placed in the CS, in order to measures a stable reference EP signal.

In order to maintain an accurate reference EP signal, it is important that the CS catheter remains fixed in-place. Any unintended CS catheter movement along the CS impacts the quality of the reference annotation and can cause inconsistencies in the electro-anatomical maps. Embodiments of the present invention that are described hereinafter provide methods and systems to verify and/or correct a placement position of the reference catheter, e.g., a CS catheter, along the CS (e.g., to compensate for possible displacement of the CS catheter), for example, during an EP mapping session. For that purpose, the disclosed embodiments produce position signals indicative of a position of the reference catheter by performing electrical measurements between the reference catheter and electrodes on the body. The electrical measurements may comprise measurements of currents, voltages and/or impedances.

In the description hereinafter, an Active Current Location (ACL) impedance-based system and technique, made by Biosense-Webster (Irvine, Calif.), serves as an example of an impedance-based position tracking system that is further configured to perform EP mapping, and this mapping-catheter using multiple electrodes is named hereinafter "ACL catheter." The body surface electrodes are named hereinafter "ACL patches." Examples of mapping-catheters are the Lasso® and Pentaray® catheters, made by Biosense-Webster. Examples of CS catheters typically used for referencing the signals that a mapping-catheter acquires are the CS Uni-Directional® and the CS Bi-Directional® Catheters, also made by Biosense-Webster.

In some embodiments, the disclosed technique includes receiving in a processor (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS. Next, the processor calculates an EP map of at least part of the heart, by time-referencing the ECG signals relative to the reference ECG signal. Based on the position signals, the processor estimates a displacement of the reference catheter from the nominal location in the CS, which distorts the time-referencing, mitigates the distortion in the EP map using the estimated displacement.

In some embodiments, two or more electrodes of the CS catheter inject electrical current to the CS tissue, and the ACL system measures the currents acquired by six ACL patch electrodes. If the CS catheter does not move, these six currents maintain a relatively constant pattern, or ratio, between themselves. If there is movement, the pattern is disturbed (i.e., changes). If the movement stops, a new constant pattern is formed. Embodiments of the present invention use the change of electrical current pattern to indicate the presence of movement. In addition, based on a calibration, embodiments of the present invention determine, from the changed currents, a magnitude of the CS catheter shift, e.g., in millimeters, as well as a direction along the CS for the shift.

In some embodiments, a processor uses an empirical formula that translates current measurements to location in order to calculate the CS catheter shift. The formula is based on known mechanical values of the CS catheter, and has several parameters that are optimized to give the same computed interelectrode distances as the real ones. In some embodiments, the calculation is optimized (e.g., calibrated) at some early stage of the mapping procedure, when the CS catheter is already in place in the CS. The calibration uses the known distance between at least one pair of electrodes of the CS catheter.

In some embodiments the processor visually presents the calculated shifted values of the CS catheter movement, and such a visual presentation assists the physician in compensating (e.g., correcting) any CS catheter movement, for example, by moving the CS catheter back to the nominal location. In another embodiment, the processor compensates for a displacement of the CS catheter by adapting the EP measurements to the displaced location of the CS catheter. In an embodiment, mitigating the distortion in the EP map includes adapting the ECG signals, or the EP map, to compensate for the displacement of the reference catheter.

Typically, the processor is programmed in software containing a particular algorithm that enables the processor to conduct each of the processor related steps and functions outlined above.

The disclosed CS catheter movement detection technique provides means to control, in real-time, the EP referencing of an EP mapping. Therefore, the disclosed technique may improve the diagnostic quality of catheter-based EP mapping procedures. By virtue of the improved mapping quality, the disclosed technique can also be used for better identifying and mitigating distortions in the EP map, such as aberrant EP activation patterns (e.g., indicative of an arrhythmia), which may otherwise be incorrectly identified, potentially leading to an ablation at a wrong location.

System Description

FIG. 1 is a schematic, pictorial illustration of an electrophysiological (EP) mapping system 20, in accordance with an embodiment of the present invention. System 20 is used for generating an EP map of at least part of a patient heart using a mapping catheter 32 and a coronary sinus (CS) catheter 50 (seen in an inset 25). CS catheter 50 is fitted at a distal end of a shaft 22. As seen, CS catheter 50 incorporates sensing-electrodes 55.

CS catheter 50 is inserted through a sheath 23 into the CS of a heart 26. Physician 30 navigates CS catheter 50 to a target location along the inside of the CS by manipulating shaft 22 using a manipulator near the proximal end of the catheter and/or deflection from the sheath 23.

CS catheter 50 is used for time referencing or propagating electrical potentials in the heart in order to produce an accurate EP map. In parallel, a mapping-catheter (not shown) moves inside heart 26 and acquires the EP potentials referenced using the EP signal acquired by CS catheter 50. As noted above, in order for CS catheter 50 to acquire meaningful reference signals, the catheter has to be kept in one place along the CS during the mapping session.

Two or more sensing-electrodes 55 are connected by wires running through shaft 22 to driver circuitry in a console 24. Console 24 comprises a processor 41, typically a general-purpose computer, with suitable front end and electrical interface circuits 37 for receiving signals from ACL patches 49. Processor 41 is connected to ACL patches 49, which are attached to the chest skin of patient 26, by wires running through a cable 39.

In some embodiments, processor 41 accurately determines a change in the position of sensing-electrodes 55 along the inside of the CS, as described below. Processor 41 determines the change in position based on, among other inputs, measured currents between sensing-electrodes 55 (on the CS catheter) and ACL patches 49 (i.e., based on injecting electrical current as described above). Console 24 drives a display 27, which shows the distal end of catheter position change relative to a nominal position along the CS, that physician 30 selected for use for referencing an EP mapping.

The method of electrode position sensing using system is implemented in various medical applications, for example in the CARTO™ system, produced by Biosense Webster and is described in detail in U.S. Pat. Nos. 8,456,182, 7,756,576, 7,869,865, and 7,848,787, whose disclosures are all incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps, as described below.

The elements of system 20 and the methods described herein may be performed by applying a voltage gradient using ACL patch electrodes 49 or other skin-attached electrodes, and measuring the potential voltage with sensing electrodes 55 on CS catheter 50. (e.g., using the Carto®4 technology produced by Biosense Webster). Thus, embodiments of the present invention apply to any position-sensing method used for EP mapping in which a sensing-electrode generates signals indicative of its position in the heart.

Coronary Sinus (CS) Catheter Movement Detection

FIG. 2 is a schematic detail view showing mapping catheter 32 and coronary sinus (CS) catheter 50 inside heart 26, in accordance with an embodiment of the present invention.

FIG. 2 shows PENTARY® mapping catheter 32 having mapping-electrodes 33 inside left atrium 34 in order to EP map the atrium. CS catheter 50 is seen in three different positions along the inside of coronary sinus 60. Any lateral shift between positions of CS catheter 50 (i.e., over a cross-section of the CS) is negligible, and is illustrated larger in FIG. 2 only for clarity of presentation.

Of the three locations along the CS, location 64 is a "nominal" (i.e., a selected) location where physician 30 initially positions catheter 50. During the EP mapping, CS catheter 50 may be displaced from its nominal position 64 distally by an amount $\Delta_1$, to a position 62, or proximally by an amount $\Delta_2$, to a position 66.

As noted above, such displacements may result in degraded quality of the reference annotation based on the EP signal acquired by two or more electrodes of CS catheter 50, such as electrodes 55, and can cause inconsistencies in the electro-anatomical maps generated based on signals acquired by mapping-electrodes 33 and referenced by respective signals acquired by sensing-electrodes 55 of CS catheter 50.

The catheter configuration described in FIG. 2 is chosen purely for the sake of conceptual clarity. Other devices on CS catheter 50, such as additional electrodes, and other sensors, such as contact force sensors, are not described.

Figure 3A:
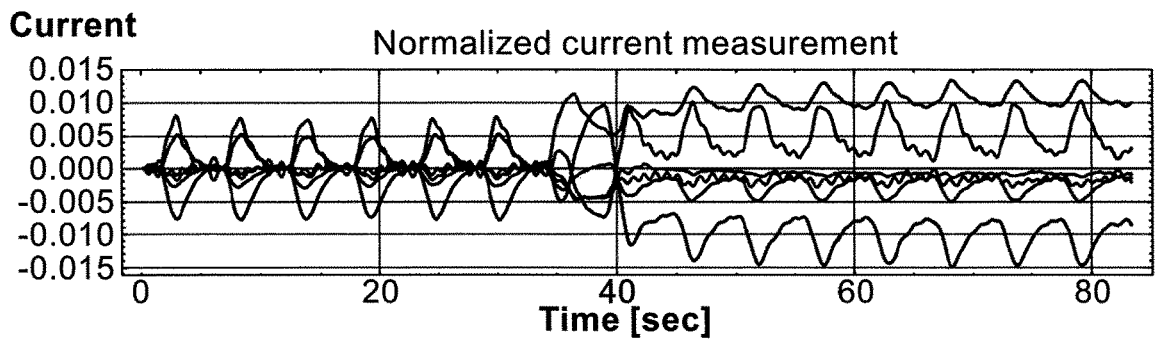
FIGS. 3A and 3B are graphs of measured ACL currents vs. time and of respective estimated movements of the catheter of FIG. 2, in accordance with an embodiment of the present invention.
Figure 3B:
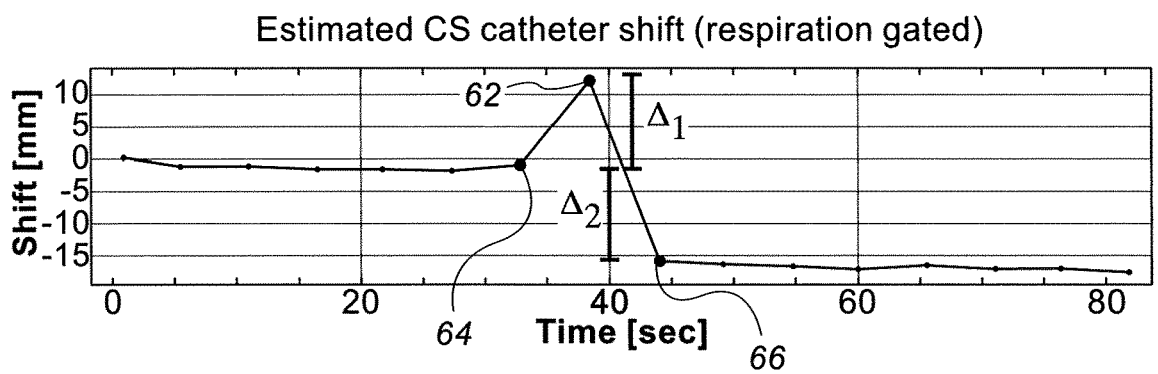

FIGS. 3A and 3B are graphs of measured ACL currents vs. time and of respective estimated movements of the catheter of FIG. 2, in accordance with an embodiment of the present invention. As FIG. 3A shows, while CS catheter 50 is stably located in its nominal position 64 between the times of 0 s and 30 s, the six currents received by ACL patches 49 maintain a relatively constant pattern, or ratio, between themselves. When CS catheter 50 moves, e.g., first distally to location 62, as illustrated in the 30 s-40 s region of the FIG. 3A, the pattern is disturbed. If the movement stops, e.g., at location 66 proximal to location 64, a new constant pattern forms, as illustrated in the times 45 s and onward.

FIG. 3B shows CS catheter displacements $\Delta_1$ and $\Delta_2$ along CS 60 that processor 41 calculates based on the signals of FIG. 3A. Processor 41 calculates the magnitude of the displacement in millimeters, as well as providing a direction along the CS for the shift. For the calculation, processor 41 uses an empirical formula (e.g., based on calibration) that translates ACL current measurements to shifts in locations.

The disclosed empirical model states that the normalized current measured by an ACL patch 49k is equal to normalized reciprocals of adjusted distances of electrode 55 to ACL patches 49:

$$\frac{I_k}{\sum_j I_j} = \frac{1/(|\vec{x}-\vec{p}_k|+a_k)}{\sum_j 1/(|\vec{x}-\vec{p}_j|+a_j)} \qquad \text{Eq. 1}$$

where $\vec{x}$—Electrode 55 position (unknown)

$\vec{p}_k$—Position of ACL patch 49 number k (ACL patches have magnetic location sensors)

$a_k$—Distance adjustment parameter (will be optimized)

$I_k$—Current measured at an ACL patch 49 number k

Given the parameters $a_k$, patch positions $\vec{p}_k$, and current measurements $I_k$, we calculate electrode 55 position by optimization:

$$\vec{x} = \underset{\vec{x}}{\operatorname{argmin}} \sum_k \left( \frac{I_k}{\sum_j I_j} - \frac{1/(|\vec{x}-\vec{p}_k|+a_k)}{\sum_j 1/(|\vec{x}-\vec{p}_j|+a_j)} \right)^2 \qquad \text{Eq. 2}$$

For simplicity the above formula is written as:

$$\vec{x} = F(I_k, \vec{p}_k; a_k) \qquad \text{Eq. 3}$$

To use the above formula, processor 41 need as inputs the parameters $a_k$, which are found using the known distances between pairs of electrodes on the catheter: $D_{m,n}$—known distance between electrodes m and n. The parameters $a_k$ are the result of the following optimization:

$$\operatorname*{argmin}_{a_k} \sum_{(m,n)\in\{ep\}} (|F(I_k^m, \vec{p}_k; a_k) - F(I_k^n, \vec{p}_k; a_k)| - D_{m,n})^2 \quad \text{Eq. 4}$$

subject to constraints on $a_k$. {ep} is the group of electrode pairs.

Where $I_k^m$ and $I_k^n$ are the currents measured at patch number k from electrodes m and n respectively.

In an embodiment, the constraint used is that all $a_k$ are equal ($a_1=a_2=a_3=a_4=a_5=a_6$).

Alternatively, other constraints over $a_k$ may be used.

The above formula is based on known mechanical values of CS catheter 50, and has several parameters that are optimized to give the same computed interelectrode distances as the real ones. The optimization happens at some early stage of an EP mapping procedure, when the CS catheter is already in location 64.

Figure 4:
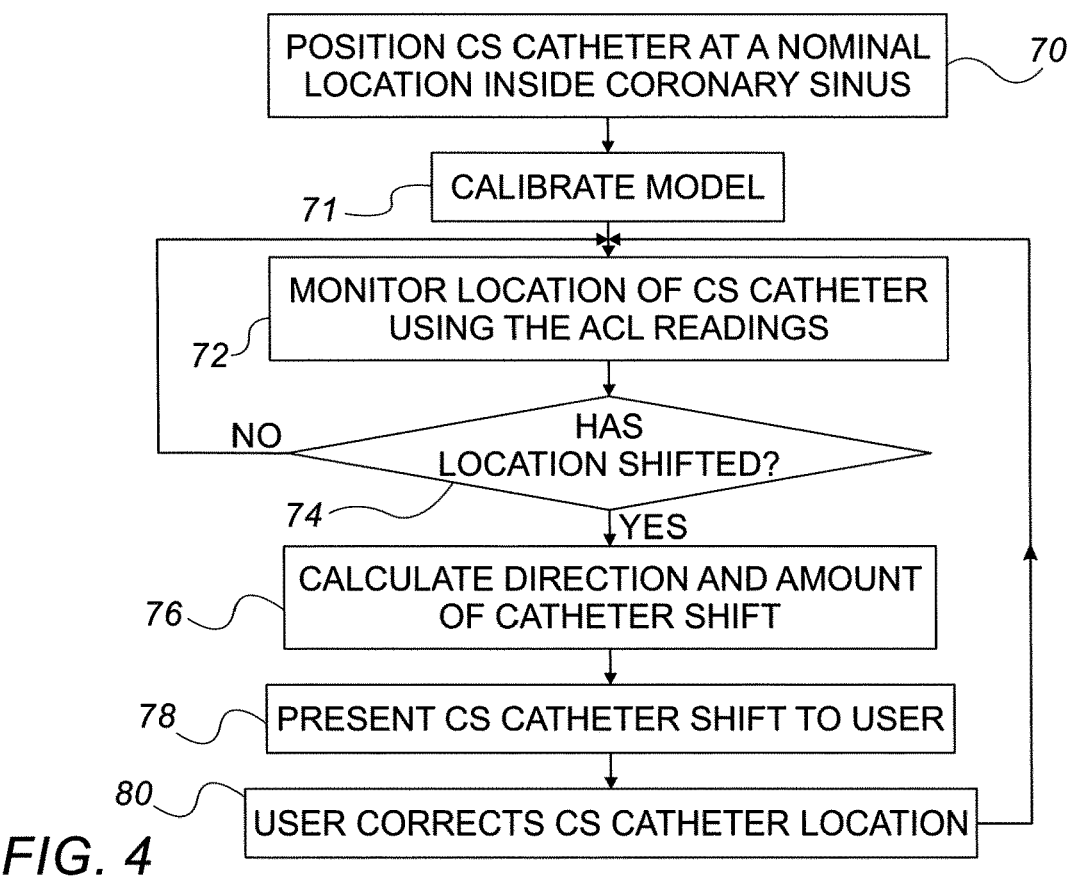
FIG. 4 is a flow chart that schematically illustrates a method and algorithm for correcting the position of the CS catheter along the coronary sinus, in accordance with an embodiment of the present invention.

FIG. 4 is a flow chart that schematically illustrates a method and algorithm for correcting the position of CS catheter 50 along coronary sinus 60, in accordance with an embodiment of the present invention. The algorithm, according to embodiments of the present invention, drives a process that begins with physician 30 positioning CS catheter 50 at nominal location 64 inside CS 60, at a CS catheter positioning step 70. Next, after the catheter is in nominal position, the disclosed model (i.e., Eq. 2) is calibrated at a calibration step 71, using the known distances between pairs of electrodes 55, to find the parameters $a_k$ is done one time—once parameters $a_k$ are found, they are fixed.

Next, based on reading ACL currents that electrodes injects and are read by ACL patches 49, which are indicative CS catheter position (i.e., position signals), processor 41, using the dedicated algorithm, monitors the location of CS catheter 50, at a CS catheter location monitoring step 72.

At a checking step 74, processor 41 checks if the location of CS catheter 50 inside CS 60 has shifted. Processor 41 uses the parameters $a_k$ to estimate the position of electrodes 55 and detect shifts of the catheter shaft position along the CS.

If the location remains the same (i.e., nominal location 64), then the process returns to location monitoring step 72. If processor 41 identifies that the location of CS catheter 50 has shifted from nominal location 64, then processor 41 calculates, using the disclosed dedicated algorithm, the direction and the amount of the shift, at a catheter shift calculation step 76. Processor 41 then presents to physician 30 the direction and amount of shift, at a presenting step 78. Next, physician 30 corrects the catheter location (e.g., brings it back to nominal location 64), at a CS catheter location correction step 80. The process then loops back to location monitoring step 72.

The example algorithm shown in FIG. 4 is chosen purely for the sake of conceptual clarity. Embodiments of the present invention also comprises additional steps of the algorithm, which have been omitted from the disclosure herein purposely in order to provide a more simplified flow chart. For example, in alternative embodiments, additional steps may be used, such as magnetic sensing of the CS catheter position.

Although the embodiments described herein mainly address cardiac EP mapping, the methods and systems described herein can also be used in other applications, such as in neurology.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for electrophysiological mapping, comprising:

receiving (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS;

calculating an electrophysiological (EP) map of at least part of the heart, by time-referencing the ECG signals relative to the reference ECG signal;

based on the position signals, estimating a displacement of the reference catheter from the nominal location in the CS utilizing fixed body electrodes, which distorts the time-referencing; and mitigating the distortion in the EP map using the estimated displacement to correct the position of the reference catheter and provide a new reference signal.

2. The method according to claim 1, and comprising producing the position signals by performing electrical measurements between the reference catheter and multiple electrodes attached to the body of the patient.

3. The method according to claim 2, wherein performing the electrical measurement comprises performing one of current measurements, voltage measurements, and impedance measurements.

4. The method according to claim 2, wherein estimating the displacement comprises calculating the displacement using an empirical formula that translates the electrical measurements to the displacement.

5. The method according to claim 1, and comprising presenting to a user a magnitude and a direction of the displacement.

6. The method according to claim 1, wherein mitigating the distortion comprises prompting a user to move the reference catheter to the nominal location.

7. The method according to claim 1, wherein mitigating the distortion comprises adapting the ECG signals, or the EP map, to compensate for the displacement of the reference catheter.

8. A system for electrophysiological mapping, comprising:

an electrical interface, configured to receive (i) a plurality of electrocardiogram (ECG) signals acquired by a mapping catheter at a plurality of locations on a surface of a heart of a patient, (ii) a reference ECG signal from a reference catheter positioned at a nominal location in a coronary sinus (CS) of the patient, and (iii) position signals indicative of a position of the reference catheter in the CS; and a processor, which is configured to:

calculate an electrophysiological (EP) map of at least part of the heart, by time-referencing the ECG signals relative to the reference ECG signal;

based on the position signals, estimate a displacement of the reference catheter from the nominal location in the CS utilizing fixed body electrodes, which distorts the time-referencing; and mitigate the distortion in the EP map using the estimated displacement to correct the position of the reference catheter and provide a new reference signal.

9. The system according to claim 8, wherein the electrical interface is configured to receive the position signals from electrical measurements performed between the reference catheter and multiple electrodes attached to the body of the patient.

10. The system according to claim 9, wherein the electrical interface is configured to receive electrical measurements comprising one of current measurements, voltage measurements, and impedance measurements.

11. The system according to claim 9, wherein the processor is configured to calculate the displacement using an empirical formula that translates the electrical measurements to the displacement.

12. The system according to claim 8, wherein the processor is further configured to present to a user a magnitude and a direction of the displacement.

13. The system according to claim 8, wherein the processor is configured to mitigate the distortion by prompting a user to move the reference catheter to the nominal location.

14. The system according to claim 8, wherein the processor is configured to mitigate the distortion by adapting the ECG signals, or the EP map, to compensate for the displacement of the reference catheter.

* * * * *